United States Patent
Liccardo et al.

(10) Patent No.: US 7,895,056 B2
(45) Date of Patent: Feb. 22, 2011

(54) SYSTEM AND METHOD FOR AUTOMATICALLY SWITCHING PRESCRIPTIONS IN A RETAIL PHARMACY TO A NEW GENERIC DRUG MANUFACTURER

(75) Inventors: Peter Liccardo, Evanston, IL (US); Casey L. Handal, Barrington, IL (US); Sam Libo, Deerfield, IL (US)

(73) Assignee: Walgreen Co., Deerfield, IL (US)

( * ) Notice: Subject to any disclaimer, the term of this patent is extended or adjusted under 35 U.S.C. 154(b) by 1025 days.

(21) Appl. No.: 11/712,736

(22) Filed: Mar. 1, 2007

(65) Prior Publication Data

US 2008/0215359 A1 Sep. 4, 2008

(51) Int. Cl.
*G06Q 10/00* (2006.01)
*G06Q 50/00* (2006.01)

(52) U.S. Cl. .................. 705/2; 705/3; 705/4; 235/375; 235/385

(58) Field of Classification Search .................. 705/2–4; 235/375, 385; 600/300; 358/43; 700/237
See application file for complete search history.

(56) References Cited

U.S. PATENT DOCUMENTS

| | | | |
|---|---|---|---|
| 6,003,006 A * | 12/1999 | Colella et al. .................. | 705/2 |
| 2003/0144876 A1 | 7/2003 | Kosinski et al. | |
| 2003/0144884 A1 | 7/2003 | Mayaud | |
| 2004/0039599 A1 | 2/2004 | Fralic | |
| 2004/0138921 A1 * | 7/2004 | Broussard et al. .............. | 705/2 |
| 2004/0172281 A1 | 9/2004 | Stanners | |
| 2005/0060197 A1 | 3/2005 | Mayaud | |
| 2005/0065821 A1 | 3/2005 | Kalies, Jr. | |
| 2005/0144038 A1 | 6/2005 | Tamblyn et al. | |
| 2005/0261939 A1 | 11/2005 | Augspurger et al. | |

* cited by examiner

*Primary Examiner*—Linh Michelle Le
(74) *Attorney, Agent, or Firm*—Francis C. Kowalik; Marshall, Gerstein & Borun LLP

(57) ABSTRACT

An automatic manufacturer switchover function to switch a set of future new, transfer, refill, and/or copy prescriptions to a new manufacturer product for a pharmacy. Furthermore, the claimed method and system may allow for a tiered approach to a manufacturer switch by allowing a corporate entity or owner of a pharmacy network to designate a pharmacy wide preferred manufacturer (or generic product) while giving a local pharmacy the power to decide when to implement a switchover at a local level. In one embodiment, the claimed switching system and process may also provide indications to pharmacists and customers to guide a transition from one manufacturer to another, thereby preserving customer perception of quality and pharmacy reputation.

19 Claims, 12 Drawing Sheets

| Description | Warehouse Local | Display New Mfg. as local option? | New Manufacturer | Listing Description |
|---|---|---|---|---|
| Old Mfg. | Y | Y | N | Y |
| Old Mfg. | N | Y | N | N |
| Old Mfg. | Y | N | N | Not Shown |
| New Mfg. | N | N | N | Not Shown |
| Old Mfg. | Y | Y | Y | Y(NEW) |

Figure 6

Change Manufacturer Multi-Hit

| Drug Name | Total Pkg Qty | Manufacturer | WHCE | NDC |
|---|---|---|---|---|
| CHLORPROPAMIDE 250MG TABLETS | 100 | MYLAN | Y | 00378-0210-01 |
| CHLORPROPAMIDE 250MG TABLETS | 100 | PLIVA | Y(NEW) | 50111-0373-01 |
| CHLORPROPAMIDE 250MG TABLETS | 1000 | MYLAN | N | 00378-0210-10 |
| CHLORPROPAMIDE 250MG TABLETS | 1000 | SIDMAK LABS | N | 50111-0373-03 |
| DIABINESE 250MG TABLETS | 100 | PFIZER | Y | 00069-3940-66 |
| DIABINESE 250MG TABLETS | 250 | PFIZER | N | 00069-3940-71 |
| DIABINESE 250MG TABLETS | 1000 | PFIZER | N | 00069-3940-82 |

Select    Cancel

Row 1 of 7

Figure 10

| Product Review As of 9:44 AM | | | | | PTIME PAT PBR | <1HR CMD |
|---|---|---|---|---|---|---|
| TEST TEST | 01/01/1950 | 56 | M | (847)555-5555 | 200 MAIN, PLANO, IN 75025 | MQ DRE |

Drug Information

Drug Image:

| | |
|---|---|
| Drug ID: | Rx #: 367855  222  REVIEWED |
| Generic For: | SPIRONOLACTONE 25MG W/HCTZ 25MG TAB |
| QTY Disp: 55 | ALDACTAZIDE 25/25 TABLETS |
| Color 1: TAN | Side 1: 5014 |
| Color 2: | Side 2: G |
| NDC: 59762 - 5014 - 01 | Orange Book: AB  Last Fill Date: AB |

Manufacturer: GREENSTONE

Warning Message:

MEDICATION GUIDE REQUIRED ← 1101
Manufacturer has changed.

Comments

Rx:

| Profile... | Drug Info Library | View Rx... | View Compound | Patient Cmts | Accept | Reject |
|---|---|---|---|---|---|---|

Figure 11

FILL DATE 08/02/06 09:59   NO 367858-00222
                           QXG/QXG/QXG/QXG/QXG
                           LF 08/02/06
PATIENT PH (847) 914-5815
           NDC 00603-2212-21
18         MFG QUALITEST
10MG TABLETS
FILLS BEFORE 08/02/07
TABLET BY MOUTH   DAW N  CLASSRX#DAYS22
                  UEH   AAA      $9.99
                  PAY CODE

Rx Info #367858-222 on 08/02/2006
By QXG 150 CARRETERA 857 CAROLINA,
LA; AMITRIPTYLINE  10MG
TABLETS:Orig Qty:22; Orig Rem Qty:462;
G "GARY" ONE T PO D NS ROUND BLUE TABLET
Side 1: 2101

May Cause Drowsiness.
Alcohol May Intensify This
Effect. Use Care When
Operating A Car Or
Dangerous Machinery.

You Should Avoid Prolonged
DOr Excessive Exposure To
Direct And/Or Artificial
Sunlight While Taking This
Medicine.

Take Or Use This Medicine
Exactly As Directed. Do
Not Skip Doses Or
Discontinue Unless
Directed By Your Doctor.

DATA
                                    08/02/06
GARY GUO
NEED ADDRESS CHICAGO, IL 60618
AMITRIPTYLINE 10MG TABLETS
Generic for ELAVIL  10MG TABLETS
GIVE "GARY" ONE
TABLET BY MOUTH
DAILY AT BEDTIME

RX0367858-00222
QTY 22
21 REFILLS BEFORE 08/02/07
              USE BEFORE 08/02/07

150 CARRETERA 857 & STATE RD
CAROLINA, LA 00987
PH (787) 701-0808

Read The Patient Information Leaflet
That Came With This Medicine (This is the same medication you have
been getting. Color, size or shape may
appear different.) — 1201

Figure 12

SYSTEM AND METHOD FOR AUTOMATICALLY SWITCHING PRESCRIPTIONS IN A RETAIL PHARMACY TO A NEW GENERIC DRUG MANUFACTURER

FIELD OF THE INVENTION

The present invention generally relates to a process for managing prescription orders in a pharmacy computer network.

BACKGROUND

Pharmacy networks may fill a prescription with a brand pharmacy product when required by brand companies holding patent rights on that pharmacy product. Generic manufacturer pharmacy products may eventually be used to replace the brand pharmacy products when patent rights expire, however, more than one generic may be available to a particular pharmacy network. In fact, with the purchase of generic drugs often going out to bid, the number of new generic manufacturers presented to pharmacy retail networks may be increasing dramatically. When a new manufacturer is stocked in a pharmacy network warehouse and shipped to local pharmacies, existing pharmacy computer systems may not be able to efficiently manage the switching of multiple new and/or existing prescriptions to a new manufacturer. If a local pharmacy wishes to switch manufacturers for a particular pharmacy product, existing pharmacy systems may enable a per prescription switching process. This per prescription switching process is often performed manually one prescription at a time and may be limited to newly inputted prescriptions. Existing systems may generally be designed in this manner to ensure consistency of prescription service (e.g., providing a customer the same product) and thereby provide a perception of quality and integrity (e.g., because generics may look different, even though the product is effectively equivalent, customers may perceive a quality difference). However, because of the large number of keystrokes needed to accomplish a single manual prescription switch and the volume of prescriptions generated and/or filled per pharmacy in a pharmacy network, manually switching prescriptions when new manufacturers of equivalent pharmacy products arrive may be a time consuming and resource draining task.

SUMMARY OF THE INVENTION

The claimed method and system provides an automatic manufacturer switchover function to switch a set of future new, transfer, refill, and/or copy prescriptions to a new manufacturer product for a pharmacy. The claimed method and system provides an easy to use and consistent process for individual pharmacies in a pharmacy network to use when a pharmacy product or drug manufacturer has changed for a prescription. The claimed method and system may decrease the number of keystrokes necessary to implement a manufacturer change on a pharmacy wide or inter-pharmacy wide level. Furthermore, the claimed method and system may allow for a tiered approach to a manufacturer switch by allowing a corporate entity or owner of a pharmacy network to designate a pharmacy wide preferred manufacturer (or generic product) while giving a local pharmacy the power to decide when to implement the switchover at a local level. In one embodiment, the claimed switching system and process may also provide indications to pharmacists and customers to guide a transition from one manufacturer to another, thereby preserving customer perception of quality and pharmacy reputation.

BRIEF DESCRIPTION OF THE DRAWINGS

FIG. 6 illustrates a table of parameters that are used to determine manufacturer switching permissions;

FIG. 10 illustrates an exemplary multiple product list screen;

FIG. 11 illustrates an exemplary screen indicating to pharmacy personnel that a manufacturer change has occurred and that a customer/patient guidance process may be required; and FIG. 12 illustrates an exemplary label that may be used to indicate that a pharmacy product is the same, but appearance may be different;

DETAILED DESCRIPTION

Although the following text sets forth a detailed description of numerous different embodiments, it should be understood that the legal scope of the invention is defined by the words of the claims set forth at the end of this patent. The detailed description is to be construed as exemplary only and does not describe every possible embodiment since describing every possible embodiment would be impractical, if not impossible. Numerous alternative embodiments could be implemented, using either current technology or technology developed after the filing date of this patent, which would still fall within the scope of the claims.

It should also be understood that, unless a term is expressly defined in this patent using the sentence "As used herein, the term '_____' is hereby defined to mean . . . " or a similar sentence, there is no intent to limit the meaning of that term, either expressly or by implication, beyond its plain or ordinary meaning, and such term should not be interpreted to be limited in scope based on any statement made in any section of this patent (other than the language of the claims). To the extent that any term recited in the claims at the end of this patent is referred to in this patent in a manner consistent with a single meaning, that is done for sake of clarity only so as to not confuse the reader, and it is not intended that such claim term be limited, by implication or otherwise, to that single meaning. Finally, unless a claim element is defined by reciting the word "means" and a function without the recital of any structure, it is not intended that the scope of any claim element be interpreted based on the application of 35 U.S.C. §112, sixth paragraph.

Figure 1:
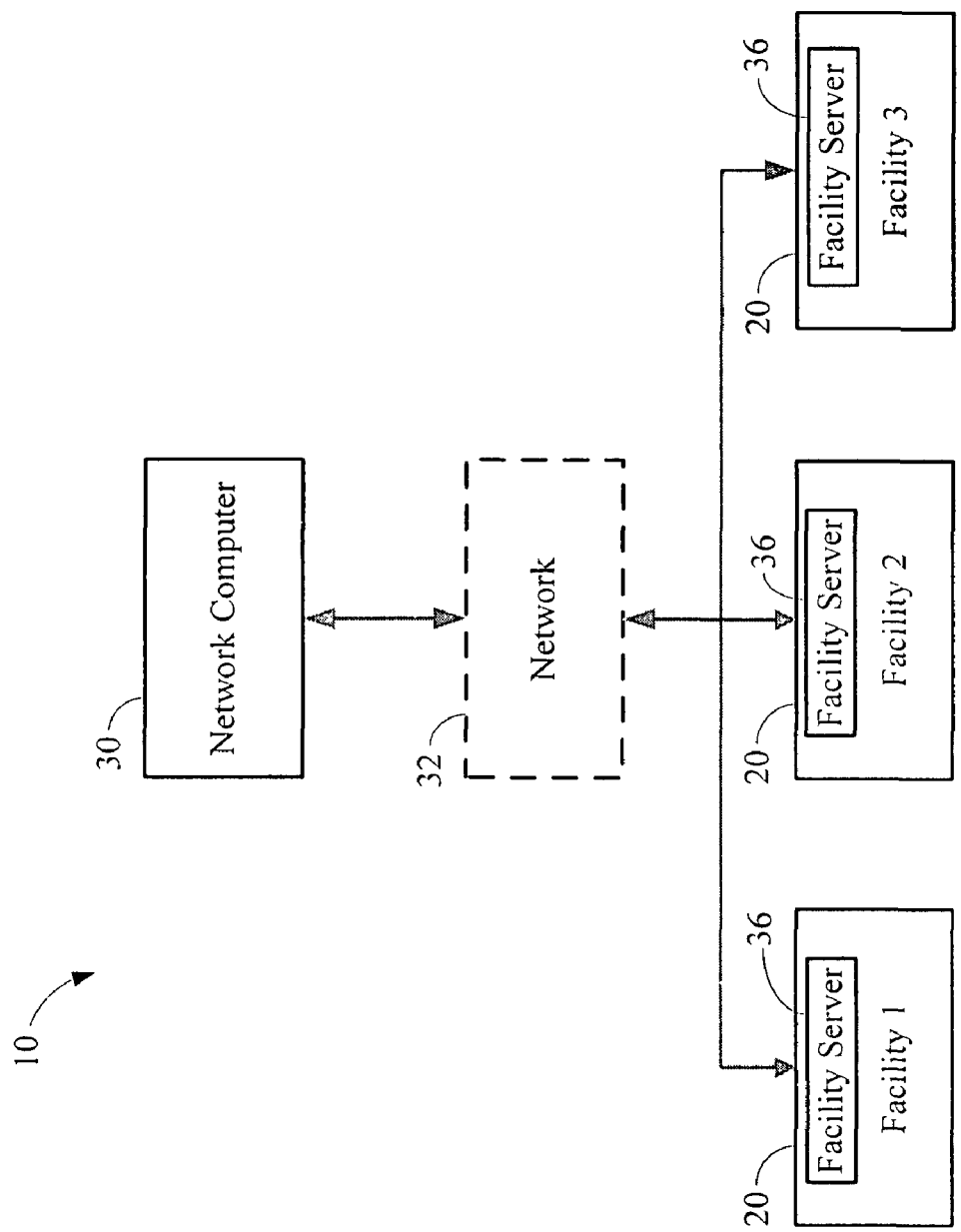
FIGS. 1-3 illustrate block diagrams of a computing system that may operate in accordance with the described embodiments.

FIG. 1 illustrates an embodiment of a data network 10 including a first group of pharmacies 20 operatively coupled to a network computer 30 via a network 32. The plurality of pharmacies 20 may be located, by way of example rather than limitation, in separate geographic locations from each other, in different areas of the same city, or in different states. The network 32 may be provided using a wide variety of techniques well known to those skilled in the art for the transfer of electronic data. For example, the network 32 may comprise dedicated access lines, plain ordinary telephone lines, satellite links, combinations of these, etc. Additionally, the network 32 may include a plurality of network computers or server computers (not shown), each of which may be operatively interconnected in a known manner. Where the network 32 comprises the Internet, data communication may take place over the network 32 via an Internet communication protocol.

The network computer 30 may be a server computer of the type commonly employed in networking solutions. The network computer 30 may be used to accumulate, analyze, and download pharmacy data. For example, the network computer 30 may periodically receive data from each of the pharmacies 20 indicative of information pertaining to a prescription order, billing information, employee data, etc. The pharmacies 20 may include one or more facility servers 36 that may be utilized to store information for a plurality of customers/employees/accounts/etc. associated with each facility.

Although the data network 10 is shown to include one network computer 30 and three pharmacies 20, it should be understood that different numbers of computers and pharmacies may be utilized. For example, the network 32 may include a plurality of network computers 30 and dozens of pharmacies 20, all of which may be interconnected via the network 32. According to the disclosed example, this configuration may provide several advantages, such as, for example, enabling near real time uploads and downloads of information as well as periodic uploads and downloads of information. This provides for a primary backup of all the information generated in the process of updating and accumulating pharmacy data.

Figure 2:
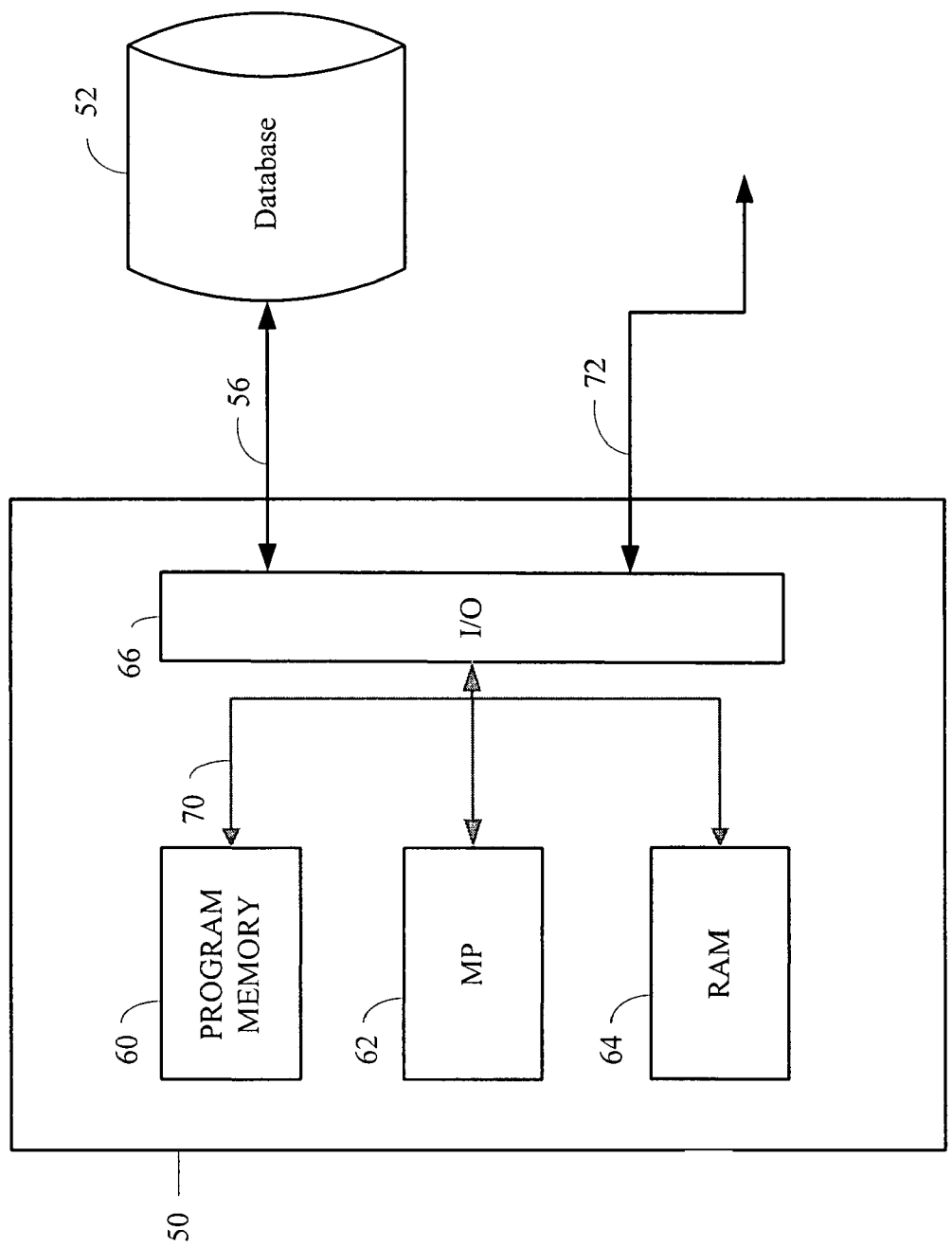

FIG. 2 is a schematic diagram of one possible embodiment of the network computer 30 shown in FIG. 1. The network computer 30 may have a controller 50 that is operatively connected to a database 52 via a link 56. It should be noted that, while not shown, additional databases may be linked to the controller 50 in a known manner.

The controller 50 may include a program memory 60, a microcontroller or a microprocessor (MP) 62, a random-access memory (RAM) 64, and an input/output (I/O) circuit 66, all of which may be interconnected via an address/data bus 70. It should be appreciated that although only one microprocessor 62 is shown, the controller 50 may include multiple microprocessors 62. Similarly, the memory of the controller 50 may include multiple RAMs 64 and multiple program memories 60. Although the I/O circuit 66 is shown as a single block, it should be appreciated that the I/O circuit 66 may include a number of different types of I/O circuits. The RAM(s) 64 and programs memories 60 may be implemented as semiconductor memories, magnetically readable memories, and/or optically readable memories, for example. The controller 50 may also be operatively connected to the network 32 via a link 72.

Figure 3:
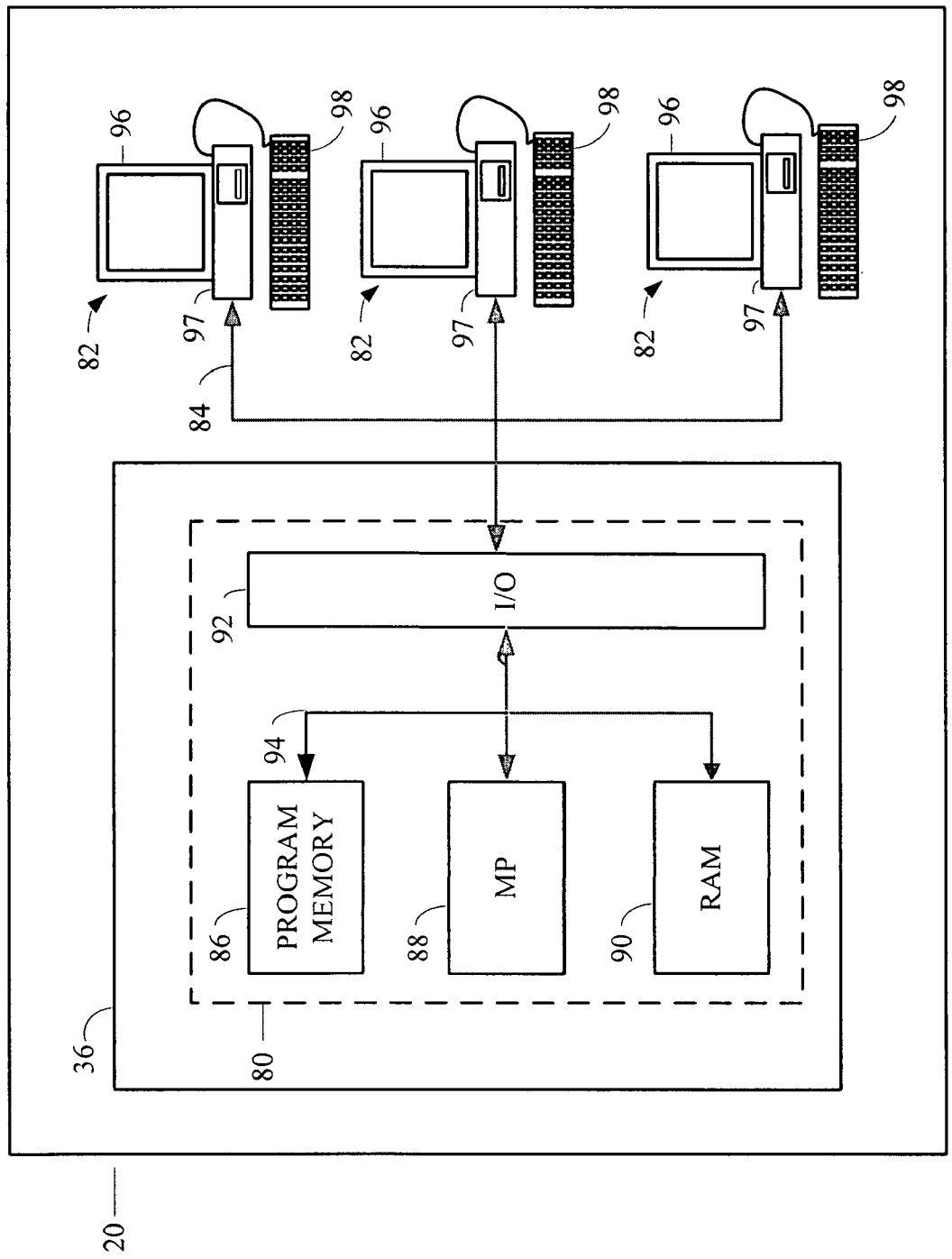

FIG. 3 is a schematic diagram of one possible embodiment of several components located in one or more of the pharmacies 20 from FIG. 1. Although the following description addresses the design of the pharmacies 20, it should be understood that the design of one or more of the pharmacies 20 may be different than the design of other pharmacies 20. Also, each pharmacy 20 may have various different structures and methods of operation. It should also be understood that the embodiment shown in FIG. 3 illustrates some of the components and data connections present in a pharmacy, however it does not illustrate all of the data connections present in a typical pharmacy. For exemplary purposes, one design of a pharmacy is described below, but it should be understood that numerous other designs may be utilized.

The pharmacies 20 may have a facility server 36, which includes a controller 80, wherein the facility server 36 is operatively connected to a plurality of client device terminals 82 via a network 84. The network 84 may be a wide area network (WAN), a local area network (LAN), or any other type of network readily known to those persons skilled in the art. The client device terminals 82 may also be operatively connected to the network computer 30 from FIG. 1 via the network 32.

Similar to the controller 50 from FIG. 2, the controller 80 may include a program memory 86, a microcontroller or a microprocessor (MP) 88, a random-access memory (RAM) 90, and an input/output (I/O) circuit 92, all of which may be interconnected via an address/data bus 94. As discussed with reference to the controller 50, it should be appreciated that although only one microprocessor 88 is shown, the controller 80 may include multiple microprocessors 88. Similarly, the memory of the controller 80 may include multiple RAMs 90 and multiple programs memories 86. Although the I/O circuit 92 is shown as a single block, the I/O circuit 92 may include a number of different types of I/O circuits. The RAM(s) 90 and programs memories 86 may also be implemented as semiconductor memories, magnetically readable memories, and/or optically readable memories, for example.

The client device terminals 82 may include a display 96, a controller 97, a keyboard 98 as well as a variety of other input/output devices (not shown) such as a scanner, printer, mouse, touch screen, track pad, track ball, isopoint, voice recognition system, etc. Each client device terminal 82 may be signed onto and occupied by a pharmacy employee to assist them in performing their duties. Pharmacy employees may sign onto a client device terminal 82 using any generically available technique, such as entering a user name and password. If a pharmacy employee is required to sign onto a client device terminal 82, this information may be passed via the link 84 to the facility server 36, so that the controller 80 will be able to identify which pharmacy employees are signed onto the system and which client device terminals 82 the employees are signed onto. This may be useful in monitoring the pharmacy employees' productivity.

Typically, facility servers 36 store a plurality of files, programs, and other data for use by the client device terminals 82 and the network computer 30. One facility server 36 may handle requests for data from a large number of client device terminals 82. Accordingly, each facility server 36 may typically comprise a high end computer with a large storage capacity, one or more fast microprocessors, and one or more high speed network connections. Conversely, relative to a typical facility server 36, each client device terminal 82 may typically include less storage capacity, a single microprocessor, and a single network connection.

Figure 4:
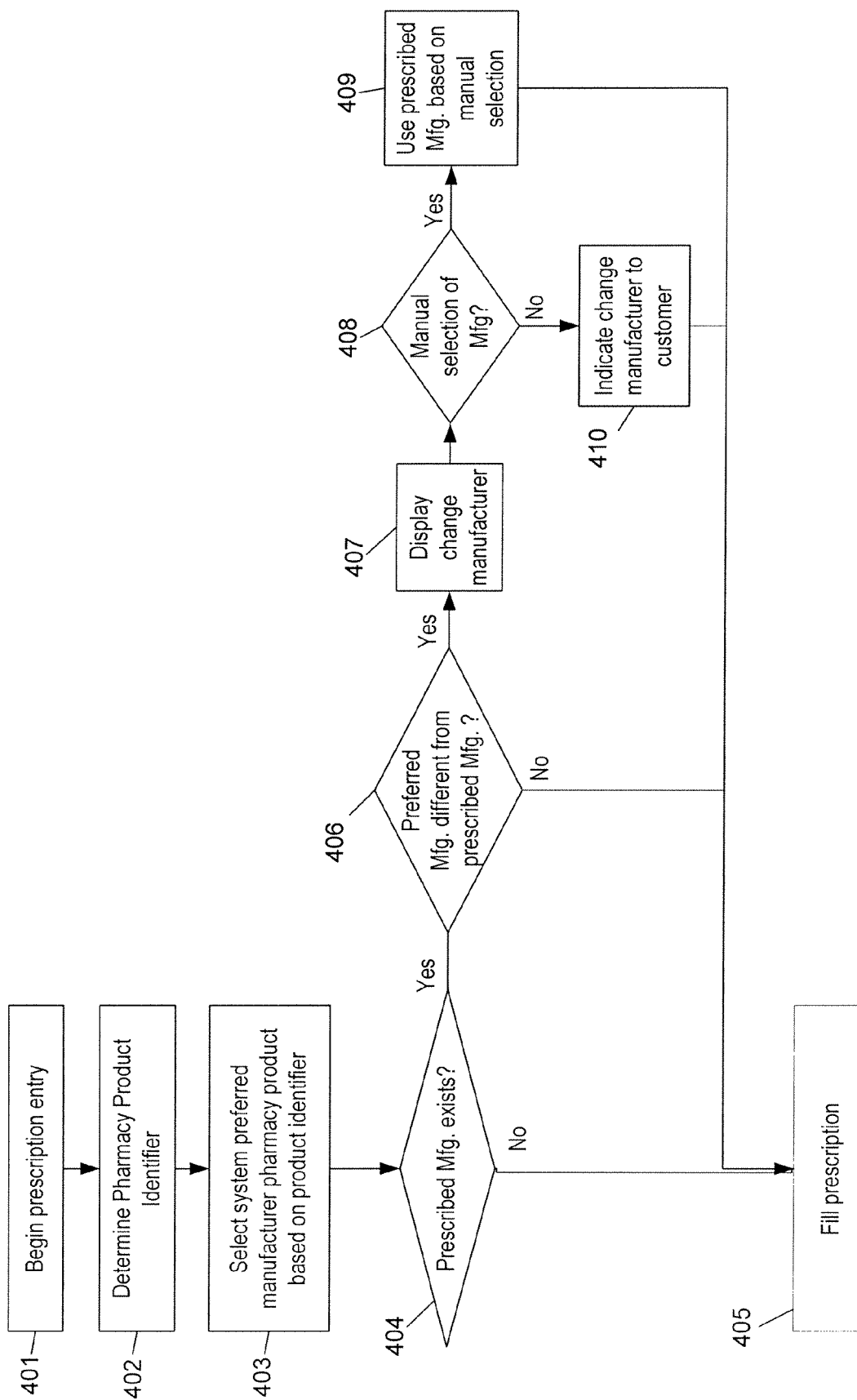
FIG. 4 illustrates an exemplary pharmacy computer system prescription entry process.

FIG. 4 illustrates an exemplary pharmacy computer system prescription entry process. In this system, a pharmacy agent or user may begin entering various prescription information into the computer system 401. In the prescription entry process, a pharmacy product identifier may be used to select a pharmacy product for filling the prescription 402. This product identifier may correspond to a pharmacy product type (e.g., a drug or medication) that has a single manufacturer (e.g., a brand manufacturer) or multiple manufacturers (e.g., generic and/or brand manufacturers). It is important to note that the pharmacy product identifier may uniquely identify a single pharmacy product type. While the single product type may be produced by different manufacturers and packaged differently (e.g., different colors, labels, boxes, containers, etc.), the products having the same product identifier may be equivalent.

Figure 9:
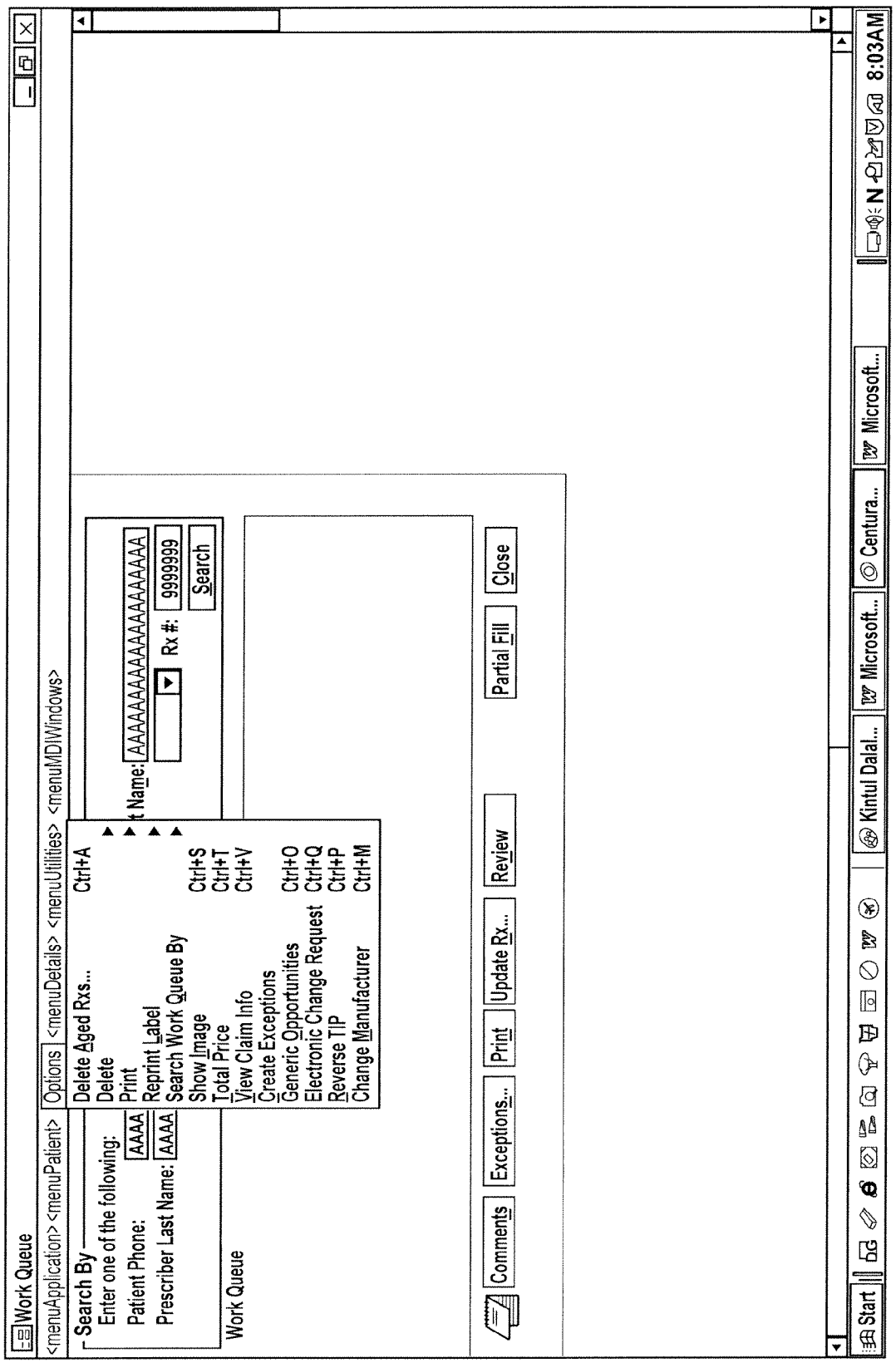
FIG. 9 illustrates a change manufacturer screen.

When the product identifier is associated with only a single manufacturer, the prescription entry portion of a pharmacy system may simply select (by default) the single manufacturer product for filling the prescription. In cases in which there exist multiple manufacturers for a single pharmacy product, the pharmacy system may provide a list of pharmacy product equivalents that are produced by different manufacturers. An example of an equivalent product list is illustrated in FIG. 10. In one embodiment, the pharmacy system may select, by default, a preferred manufacturer product for a particular pharmacy product identifier when there exists multiple manufacturers 403. In this embodiment, if there are no customer or physician designated manufacturers 404, the preferred manufacturer product may be filled 405 using the selected default whenever the associated pharmacy product identifier is entered for a prescription. Also, if a pharmacy agent needs to change the manufacturer, a change manufacturer screen may be used, as illustrated in FIG. 9.

In cases in which there exist multiple manufacturers for a single pharmacy product, a physician may prescribe a preferred manufacturer for the pharmacy product. For example, in one embodiment, a pharmacy agent inputting a prescription may enter a national drug code (NDC) number that specifies the pharmacy product (e.g., a pharmacy product identifier) and a manufacturer of the pharmacy product. In one embodiment, after entering an NDC code specific to a pharmacy product and manufacturer of the pharmacy product, the pharmacy system may determine whether the designated manufacturer differs from the system preferred manufacturer 406. If there is a difference, a change manufacturer indication may be displayed 407 to a pharmacy agent. If there is no manual selection or affirmation of a prescribed manufacturer 408, the pharmacy system may fill the prescription 405 using the preferred manufacturer designated by the pharmacy system instead of the prescribed manufacturer from the NDC 409. This may be done to provide a cost savings to a customer for an equivalent generic product. In this case, if the preferred manufacturer differs from a prescribed manufacturer 406, indications may be provided to customers that a manufacturer change has occurred 410 (to be discussed further below). In a further embodiment, while the pharmacy system may automatically select the system preferred manufacturer, the pharmacy system may allow pharmacy personnel to select the NDC manufacturer 409 to fill the prescription 410.

Figure 5:
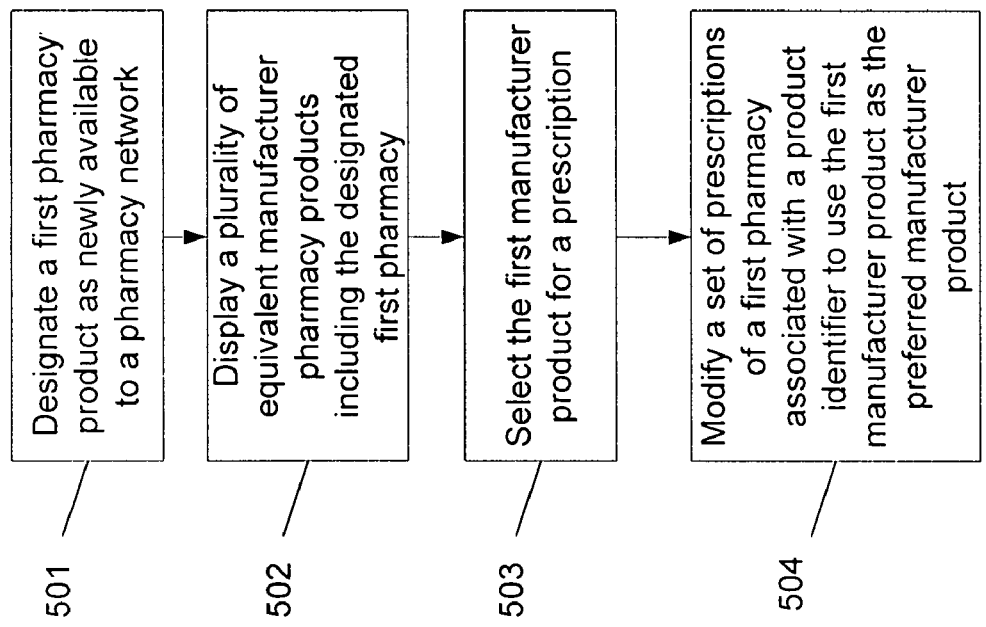
FIG. 5 illustrates an embodiment of a pharmacy switchover process that may be implemented in the pharmacy system.

FIG. 5 illustrates an embodiment of a pharmacy switchover process that may be implemented in the pharmacy system. In this embodiment, a manufacturer pharmacy product may be designated as a newly available preferred product for a pharmacy network 501. This designation may be made on a pharmacy-wide level. When a new manufacturer has been designated by, for example, a corporate parent, and other local pharmacy parameters are met (for example, inventory conditions), then a local pharmacy trigger may be configured to switch existing and/or new prescriptions at the local pharmacy to use the network designated manufacturer pharmacy product. The trigger may be set off via a manual operation such as a manual change in a single prescription order fill (at the local pharmacy) from a previously designated preferred manufacture product to the newly designated preferred manufacture product. For example, when modifying a prescription (e.g., changing an existing prescription or entering a new prescription), pharmacy personnel may bring up an options screen for a plurality of equivalent pharmacy products that have different manufacturers 502. (This options screen may be displayed only when a default preferred product is to be manually changed.) The plurality of equivalent pharmacy products may include the newly designated manufacturer pharmacy product. The newly designated manufacturer product may be highlighted in the display to indicate that it is designated as a newly available, network preferred manufacturer product (e.g., as "Y (New)," as illustrated in FIG. 6). Next a newly designated manufacturer product may be manually selected for the single prescription 503. The manual selection may set off a trigger to automatically change all prescriptions having corresponding equivalent pharmacy products to use the newly designated manufacturer product 504.

The designation of the preferred manufacturer on the pharmacy wide level may be performed by a corporate entity owning or controlling the pharmacy network. In this situation, the entity owning or controlling the pharmacy network may designate a pharmacy wide manufacturer preference for a particular pharmacy product. However, because of stocking issues for the new manufacturer pharmacy product at a local pharmacy or the need to exhaust existing supplies of old manufacturer pharmacy product, local pharmacy involvement in a manufacturer switch may be beneficial. In other words, it may be detrimental for a corporate entity to force a complete and sudden switchover to a preferred manufacturer without consideration of local pharmacy conditions. In this case, a manufacturer switch across a pharmacy network may be managed more efficiently by allowing a two stage process involving a network wide switching decision and a local pharmacy switching decision. In this manner, a pharmacy company operating a network of pharmacies may be able to take advantages of a negotiated bulk purchasing of product on a network wide scale, while allowing each pharmacy to manage the switchover on a local level to account for local conditions.

Figure 7:
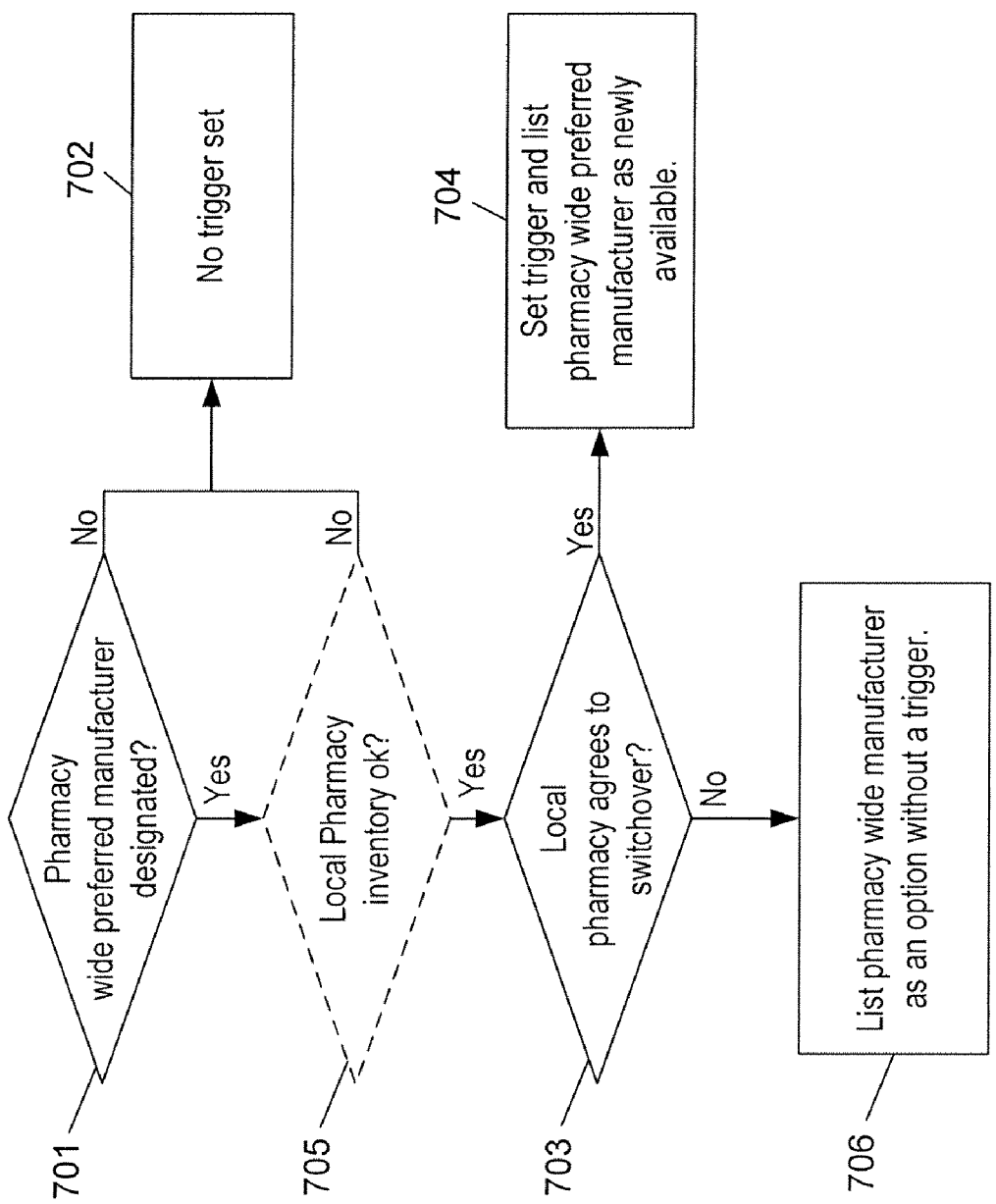
FIG. 7 illustrates a flow chart relating to activating and listing manufacturer options for a pharmacy product coinciding with the parameters of FIG. 6.

FIG. 6 illustrates a table of parameters that are used to determine manufacturer switching permissions and FIG. 7 illustrates a flow chart relating to activating and listing manufacturer options for a pharmacy product coinciding with the parameters of FIG. 6. A network wide decision may be made by setting a network wide system parameter called, e.g., "New Manufacturer" 602, to indicate a new network preferred manufacturer. If the new manufacturer is not set 701, then no trigger may be set 702. If the network sets the new manufacturer 701, then a local pharmacy on the pharmacy network may implement, at its own discretion 703, a computer configured switch (or trigger) on a local scope 704. The local scope permission may be made by setting a local parameter 606 indicating that the new manufacturer may be displayed as a local pharmacy option.

One factor that a local pharmacy may consider in determining whether or not to accept the corporate wide or network wide preferred manufacturer product is how much remaining inventory the local pharmacy has in stock of an existing preferred product 705. If there isn't sufficient inventory (e.g., past a threshold level), then no trigger may be set 702. Related to the inventory factor is whether the local pharmacy has an existing contract with a local supplier (different from a network preferred supplier) for an existing preferred product that must expire before any new equivalent products may be stocked in bulk. These factors may be integrated into setting a warehouse level parameter 608 that may determine whether the local parameter 606 may be set. If a pharmacy wide manufacturer is elected by the network 701, but the local pharmacy has not elected to enable a trigger 703, the newly designated manufacturer may simply be listed as a fill option 706, or not listed at all.

Another factor that may be included in the determination of whether the trigger listing may be displayed is whether the pharmacy product has an associated substitute drug identifier (not shown), indicating that one pharmacy product is related to another pharmacy product in such a manner as to preclude a blanket replacement with a designated preferred pharmacy product.

As further illustrated in FIG. 6, only when a local warehouse indicator 608, a local scope indicator 606, and a network wide indicator 602 are set (e.g., set to "Y"), may a "Y (NEW)" indication 614 be displayed in a pharmacy product equivalent listing 604. A previously designated preferred manufacturer may be listed as a "Y" indication 610. A non-preferred, non-stocked local pharmacy product may be listed as "N" indication 612. In one embodiment, products labeled as "N" may be special ordered.

As discussed above, the "Y (NEW)" may indicate the existence of a newly available, network wide manufacturer product. The "Y (NEW)," may also indicate that a trigger has been set to automatically change over all local pharmacy prescriptions requesting pharmacy products equivalent to the new manufacturer product upon setting off the trigger. In one embodiment, once the newly available manufacturer product has been manually selected and the automatic trigger has been set off, the manufacturer may no longer be listed as new, and may simply be designated as a preferred manufacturer product. For example, "Y(New)," may be relabeled "Y" to indicate that it is no longer a new manufacturer product, but may be the current preferred manufacturer product. In this embodiment, only a single manufacturer may be listed as the preferred manufacturer (i.e., "Y") and only one manufacturer may be designated as a newly available, potentially preferred, manufacturer (i.e., "Y (New)")

Figure 8:
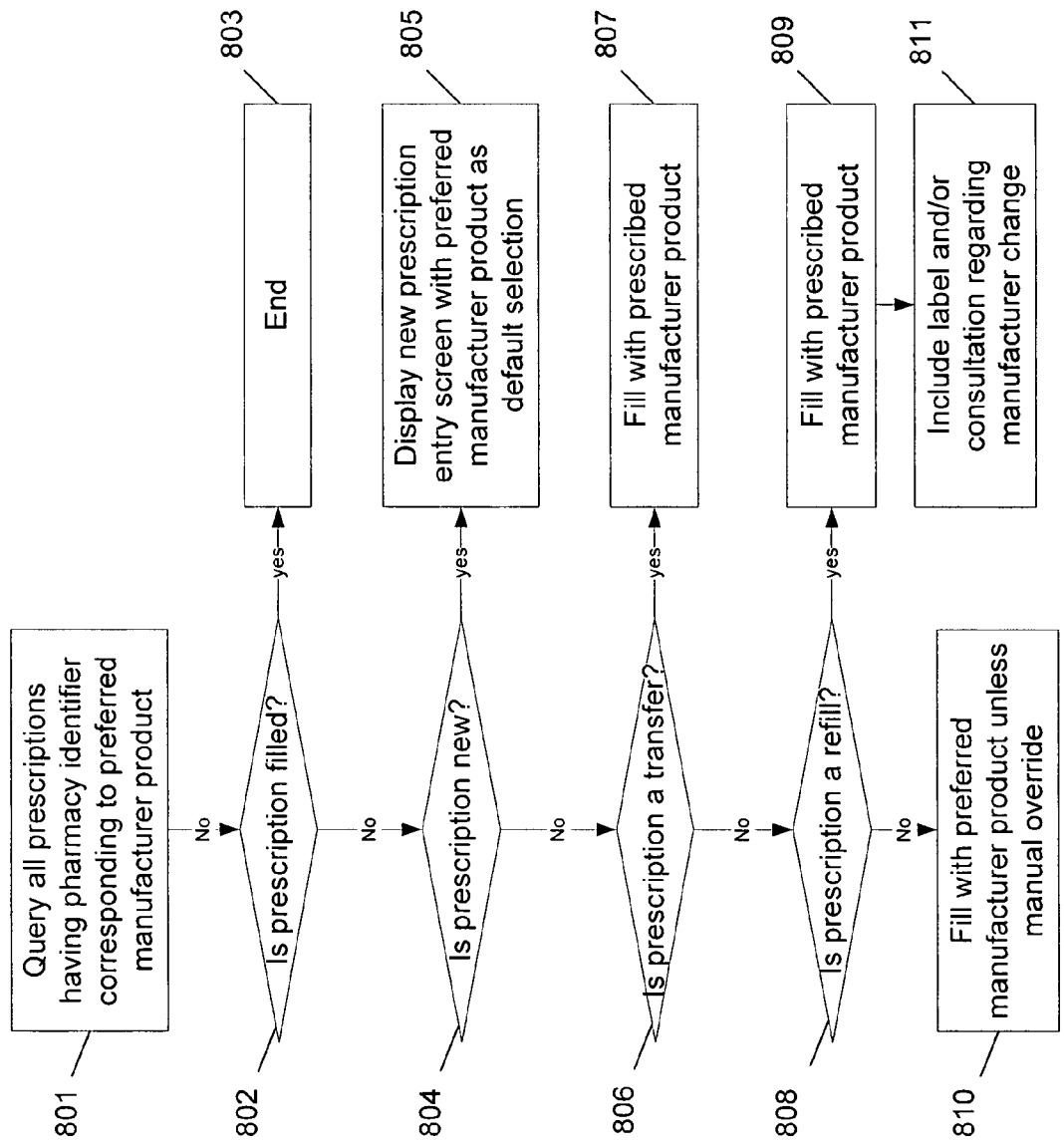
FIG. 8 illustrates a flow chart relating to trigger implementations based on prescription type.

The mechanism behind the switchover function may be implemented in a number of ways and may depend on prescription type. As illustrated in FIG. 8, the trigger may initiate a database query of all unfilled local prescriptions requesting equivalent pharmacy products corresponding to the designated pharmacy product 801. If the prescription has already been filled 802, then there may be nothing left to change 803. For existing prescriptions that have not been filled yet 802, if a new manufacturer product is designated and the switchover is triggered before the prescription has been filled, then the query can modify those prescriptions to be filled with the new manufacturer 810 (unless a pharmacy service person manually changes the prescription, as described above).

For future new prescriptions 804, the selection of a manufacturer product may default to the preferred manufacturer product 805. As discussed above, this preferred manufacturer product may be the new manufacturer pharmacy product when a pharmacy triggers the switchover. In one embodiment, this portion of the trigger may be implemented as follows. A pharmacy product identifier that corresponds to a particular pharmacy product may be associated with a preferred manufacturer product identifier that designates a manufacturer that produces the pharmacy product. In this embodiment, all future/new prescriptions that request the pharmacy product may be directed to use the newly designated manufacturer pharmacy product by modifying the preferred pharmacy product parameter to reference the newly designated first manufacturer product. As discussed above, however, the preferred pharmacy product may be manually changed, if desired.

In one embodiment, if a prescription that originated from a first retail store is to be filled at a second retail store (a transfer prescription) 806, then a pharmacy product corresponding to the prescribed prescription product may be used 807, regardless of whether a preferred manufacturer product is being used at the second store. For example, in a situation in which a customer has specifically designated a specific manufacturer product at the prescription originating pharmacy (or prescription drop-off pharmacy), prescription fills at different stores will not be changed. In this manner, inter-pharmacy inconsistencies or preferences are respected and may prevent unnecessary complications with customer expectations and instructions.

If a prescription is a refill prescription 808, then the switchover may cause the prescription to be filled with the preferred manufacturer product 809. Because switching over manufacturers may alarm customers, a managed transition process involving the clients may be implemented to alleviate any anxiety in customers and bring goodwill to a pharmacy network. In some cases, the appearance of a pharmacy product (e.g., a drug) may be different based on the manufacturer, even though for medication purposes, the drug is chemically the same. For example, first manufacturer A may make Chlorpropamide in red while a second manufacture B may produce Chlorpropamide in blue. In one embodiment, a warning label may be provided 811 indicating that the product is the same product as previously filled, but with a new manufacturer. In one embodiment, the label may also indicate that it is a generic pharmacy product and that the switchover is made to provide a customer an equivalent product for a better price. In one embodiment, a price difference between two manufacturer products (e.g., the difference between a previously filled manufacturer product and a new manufacturer product) may be shown on the label.

FIG. 11 illustrates a screen indicating to pharmacy personnel that a manufacturer change has occurred and that a customer/patient guidance process may be required 1101. FIG. 12 illustrates a label that may be used to indicate that a pharmacy product is equivalent, but that the appearance of the product may be different 1201 (as a result of a different manufacturer).

Using the above described switching process, an existing pharmacy network system that is only capable of switching one prescription at a time may be modified to switch multiple prescriptions (both existing and future prescriptions) automatically using a quicker process. This switching system may factor in a tiered decision approach to network switching that accounts for differences in local pharmacy conditions (e.g., inventory levels), thereby realizing efficiencies in product distribution timing. The switching process may also account for differences in prescription type that may make it difficult for previous systems to implement automated switching.

What is claimed:

1. A method of managing a pharmacy product manufacturer change in a pharmacy computing system comprising:

obtaining an indication that a first pharmacy manufacturer product corresponding to a pharmacy product type is designated as newly available in the pharmacy computer system, the pharmacy product type corresponding to a drug;

obtaining an indication that the first pharmacy manufacturer product is designated as a preferred manufacturer product corresponding to a pharmacy product identifier corresponding to the pharmacy product type;

displaying indications of a plurality of pharmacy product equivalents corresponding to the pharmacy product identifier, including displaying an indication of the first pharmacy manufacturer product;

receiving an indication that the first pharmacy manufacturer product is selected for filling a first prescription, the first prescription corresponding to a pharmacy location; and based on the indication that the first pharmacy manufacturer product is selected for filling the first prescription, modifying data of each of a set of unfilled prescriptions corresponding to the pharmacy location and to the pharmacy product identifier to indicate the first pharmacy manufacturer product is a current preferred manufacturer product for the each of the set of unfilled prescriptions.

2. The method of claim 1, further comprising changing the data of each of the set of unfilled prescriptions to indicate the first pharmacy manufacturer product is a default product for filling each of the set of unfilled prescriptions.

3. The method of claim 1, wherein modifying the data of each of the set of unfilled prescriptions corresponding to the pharmacy location and to the pharmacy product identifier to indicate the first pharmacy manufacturer product is the current preferred manufacturer product comprises modifying the data of each of the set of unfilled prescriptions corresponding to the pharmacy location and to the pharmacy product identifier to indicate the first pharmacy manufacturer product is the current preferred manufacturer product when an inventory of the first pharmacy manufacturer product is available to the pharmacy location.

4. The method of claim 1, further comprising allowing a user to further modify the data of one of the set of unfilled prescriptions to indicate a different pharmacy manufacturer product other than the first pharmacy manufacturer product for filling the one of the set of unfilled prescriptions.

5. The method of claim 1, wherein obtaining the indication that the first pharmacy manufacturer product is designated as newly available comprises obtaining an indication that a new manufacturer product flag is set at an inter-pharmacy level and obtaining an indication that a warehouse of a local pharmacy contains a threshold level of the first pharmacy manufacturer product.

6. The method of claim 5, wherein obtaining the indication that the first pharmacy manufacturer product is designated as newly available further comprises obtaining an indication that a preferred manufacturer indicator is set at a local pharmacy level.

7. The method of claim 1, wherein modifying the data of each of the set of unfilled prescriptions comprises setting a flag associated with the data of each of the set of unfilled prescriptions to indicate that a manufacturer change has occurred.

8. The method of claim 1, further comprising automatically setting the first pharmacy manufacturer product as a default product for filling a new prescription corresponding to the pharmacy location and corresponding to the pharmacy product identifier.

9. The method of claim 1, further comprising determining whether a warning of a manufacturer change is required and producing a label with the warning if it is determined to be required.

10. The method of claim 1, further comprising displaying a counseling screen at a point of sale computer when one of the set of unfilled prescriptions is for a refill and the current preferred manufacturer product for the one of the set of unfilled prescriptions has changed since a previous fill.

11. The method of claim 10, further comprising blocking the one of the set of unfilled prescription from being released until a patient counseling session is confirmed.

12. A computing apparatus comprising:
a display unit;
an input device;
a processing apparatus operatively coupled to the display unit and to the input device, the processing apparatus comprising a processor and a memory operatively coupled to the processor; and
a network interface connected to a network and to the processing apparatus;
the processing apparatus being programmed to:
determine, via the network interface, that a local warehouse indicator for a first pharmacy manufacturer product corresponding to a pharmacy product identifier indicates the first pharmacy manufacturer product is available at a corresponding local warehouse, and that an inter-pharmacy new product indicator indicates the first pharmacy manufacturer product is newly available, the pharmacy product identifier corresponding to a pharmacy product type corresponding to a drug;
display, on the display unit, a listing of pharmacy products corresponding to the pharmacy product identifier, the listing including the first pharmacy manufacturer product;
indicate, on the display unit and based on the local warehouse indicator and inter-pharmacy new product indicator, the first pharmacy manufacturer product as newly available; and
upon selection via the in u device of the first pharmacy manufacturer product for a prescription corresponding to a pharmacy location:
query for a set of unfilled prescriptions corresponding to the pharmacy location, each of the set of unfilled prescriptions including the pharmacy product identifier; and
modify each of the set of unfilled prescriptions resulting from the query to update an indication of a current preferred manufacturer product to indicate the first pharmacy manufacturer product.

13. The computing apparatus of claim 12, wherein the processing apparatus is further programmed to default each of the set of unfilled prescriptions to be filled with the first pharmacy manufacturer product.

14. The computer apparatus of claim 12, wherein the processing apparatus is further programmed to allow a user to select, via the input device and from the listing of pharmacy products, a different pharmacy product that is not the preferred manufacturer product for one of the set of unfilled prescriptions.

15. The computer apparatus of claim 12, wherein the processing apparatus is further programmed to set a change manufacturer indicator when the first pharmacy manufacturer product is selected.

16. The computer apparatus of claim 12, wherein the processing apparatus is further programmed to block processing of one of the set of unfilled prescriptions if the change manufacturer indicator is set.

17. The computer apparatus of claim 16, wherein the processing apparatus is further programmed to display a patient counseling screen if the change manufacturer indicator is set and if the one of the set of unfilled prescriptions is a refill prescription.

18. The computer apparatus of claim 12, wherein the processing apparatus is further programmed to select the first pharmacy manufacturer product as a default for a new prescription corresponding to the pharmacy product identifier.

19. A system for managing prescription orders comprising:
a plurality of pharmacies connected by a network computer system;
a system database accessible to the network computer system for storing a first field indicating whether a first manufacturer pharmacy product corresponding to a pharmacy product identifier corresponding to a drug is newly available for the plurality of pharmacies;
a local database accessible to the network computer system for storing a second field indicating whether a local warehouse associated with a first pharmacy of the plurality of pharmacies contains a threshold quantity of the first manufacturer pharmacy product, and the local database storing prescription data for a set of prescriptions corresponding to the first pharmacy; and
a first computer of the network computer system adapted to:

display the first pharmacy manufacturer product as a newly available product amongst a plurality of pharmacy product equivalents if the first field indicates that the first manufacturer pharmacy product is newly available and the second field indicates that the local warehouse contains the threshold quantity of the first manufacturer pharmacy product, and modify the prescription data of a subset of set of the prescriptions in the local database to indicate the first manufacturer pharmacy product is a current preferred manufacturer product for each of the subset of the set of prescriptions, the subset of the set of prescriptions corresponding to the first pharmacy and to the pharmacy product identifier.

* * * * *